United States Patent [19]

Kunig

[11] Patent Number: 4,854,327

[45] Date of Patent: Aug. 8, 1989

[54] NON-INVASIVE AND CONTINUOUS CARDIAC PERFORMANCE MONITORING DEVICE

[76] Inventor: Horst E. Kunig, P.O. Box 577, R.D. #1, Saltsburg, Pa. 15681

[21] Appl. No.: 165,018

[22] Filed: Mar. 7, 1988

[51] Int. Cl.⁴ ............................................... A61B 5/04
[52] U.S. Cl. .................................... 128/713; 128/704; 128/707
[58] Field of Search ................ 128/704, 706, 707, 713

[56] References Cited

U.S. PATENT DOCUMENTS 4,137,910  2/1979  Murphy .......................... 128/713 X
4,622,980  11/1986  Kunig ................................. 128/704

Primary Examiner—Francis Jaworski
Attorney, Agent, or Firm—Clifford A. Poff

[57] ABSTRACT

A non-invasive cardiac monitoring device for calculating the cardiac performance parameters of heartbeat, stroke volume, and cardiac output for an individual. The device receives electrocardiogram waveform signals from the individual and calculates a ratio of the R-wave component of the electrocardiogram waveform to the T-wave of the electrocardiogram waveform. From this ratio, the stroke volume of the individual and the cardiac output of the individual may be calculated. The periodicity of subsequent electrocardiogram waveforms are utilized to calculate the heartbeat of the individual.

17 Claims, 5 Drawing Sheets

NON-INVASIVE AND CONTINUOUS CARDIAC PERFORMANCE MONITORING DEVICE

BACKGROUND OF THE INVENTION

1. Field of the Invention

The present invention relates generally to monitoring devices, and, more particularly, to a non-invasive monitoring device for determining the cardiac performance of an individual.

2. Description of the Prior Art

Various means have been developed in order to quantify the cardiac performance of an individual. Two parameters are commonly obtained to quantitatively measure the individual's cardiac performance.

The first of the parameters, referred to as stroke volume, is defined as the volume of blood pumped by the individual's heart in one heartbeat. The second parameter, referred to as cardiac output, is defined as the volume of blood pumped by the individual's heart in one minute. Cardiac output, thus, is the sum of the stroke volume over sixty seconds, and, may be derived from taking the sum of an individual's stroke volume over sixty seconds.

Presently, several different invasive methods are utilized in order to obtain values for these parameters. One such method, the Fick method, determines a value for the stroke volume by determining oxygen consumption of the individual and by detecting changes in an individual's arterio-venous oxygen concentration levels. A second invasive method, the thermodilution determines a value of cardiac output through an analysis of the changes of the temperature of a cold bolus injected into the individual's circulatory system. The cold bolus, having a temperature less than that of blood, causes a temporary decrease in the temperature of the individual's heart as the bolus enters the heart chambers. Once the bolus is pumped from the heart chambers and replaced by the higher temperature blood, the temperature of the heart recovers. By measuring the amount of time required for the heart temperature to recover, the volume of blood pumped during this period of time may be calculated, such calculated value being extrapolated to produce a value of the cardiac output in sixty seconds. Instead of a cold bolus, a dye maybe injected and the stroke volume is determined from the dilution of the dye.

The use of the invasive methods of determining the stroke volume and/or cardiac output of an individual are potentially dangerous, and are frequently unable to be performed as catheters must be inserted into the heart or other parts of the circulatory system to obtain the required information. Additionally, both the Fick method and the thermodilution and dye methods, in actuality, measure the average stroke volume and/or cardiac output of an individual by measuring the amount of blood circulated over a specific period of time and dividing the measured volume by the number of heartbeats of the individual's heart during that period of time. As is inherent in any average value, the average may differ substantially from that of a single value. In this instance, the actual stroke volume associated with a single heartbeat of the individual may differ from the average as the individual's stroke volume may fluctuate considerably from heartbeat to heartbeat, depending upon the activity performed by the individual.

Three non-intensive methods of determining stroke volume are alternatively used. The first such method, the Doppler-ultrasound method, determines a value for the stroke volume of an individual by calculating the Doppler effect upon an ultra-high frequency sound wave reflected from moving blood cells. The second method, the bioimpedance method, calculates the value for stroke volume of an individual by modulating a d.c. current by a measured blood pressure wave. The third method, the echocardiography method, calculates a value for the stroke volume based upon measurements of the size of the heart chamber of the individual.

While the Doppler-ultrasound and bioimpedance methods of determining stroke volume are non-invasive procedures and incur little risk to the patient, the methods cannot be utilized when performing certain medical procedures, such as open heart surgery. For instance, in order to perform the Doppler-ultrasound method, sensors must be positioned, and often repositioned, in the esophageal and sternal areas of the individual, and in order to perform the bioimpedance method, eight electrodes must be positioned in precise locations. And the third non-invasive method, the echocardiography method, is of limited usefulness as only intermittent visualization of the heart chamber of the individual is possible. Therefore, the echocardiography method is also precluded for use during certain medical procedures, such as open heart surgery.

More recently, electrocardiogram waveform changes were utilized to determine cardiac functions. One such method is disclosed in U.S. Pat. No. 4,622,980, to H. E. Kunig, the same inventor as that of the instant invention. In this disclosure, an electrocardiogram waveform is separated into its component parts, the center spike or R-wave, the left-side sinusoidal P-wave, and the right-side sinusoidal T-wave. The electrocardiogram waveform is quantified by measuring the R-wave amplitude and the T-wave amplitude, and then calculating the ratio of the R-wave amplitude to the T-wave amplitude. The ratio is first calculated when the individual is at rest. The same ratio is then calculated subsequent to the application of a stress to the individual's cardiovascular system. The pre-stress ratio is then compared with the ratio calculated subsequent to the application of the stress. This new value is referred to as the stress index, S, and may be utilized to relate stressful events in terms of electrocardiogram waveform changes on a numerical scale.

A second method is disclosed in U.S. Pat. No. 3,572,321, to Bloomfield. In this disclosure, the R-wave amplitude and T-wave amplitude are measured, and a ratio of the two values is calculated. If the ratio is less than a certain value, a cardiac insufficiency is indicated. However, a typical electrocardiogram consists of numerous different waveforms, with a separate waveform corresponding to each of a dozen different electrodes attached at different locations on an individual's body. Because the magnitude of the ratio is dependent upon which waveform is selected, the indication of cardiac sufficiency or insufficiency is dependent, at least in part, upon which waveform is selected. However, this method is of utility as a quick indicator of cardiac performance during mass screening procedures.

It is therefore the object of the present invention to provide a means for quantitatively and non-invasively determining cardiac pumping performance of an individual.

SUMMARY OF THE INVENTION

In accordance with the present invention, a non-invasive cardiac monitoring device is disclosed for determining the cardiac performance of an individual. The monitoring device is comprised of electrocardiogram sensing means for sensing electrocardiogram waveforms of the individual and for generating signals indicative of the waveforms. An R-wave amplitude measuring means measures the amplitude of an R-wave component of the electrocardiogram waveform, and a T-wave amplitude measuring means measures the amplitude of a T-wave component of the electrocardiogram waveform. A ratio calculating means determines the ratio of the amplitude of the R-wave component to the amplitude of the T-wave component and generates a ratio signal indicative of the calculated ratio. A stroke volume calculating means generates a signal indicative of the stroke volume of the individual in response to the ratio signal generated by the ratio calculating means, and, may be calculated by the equation: Stroke Volume $(ml) = 7.5 * R/T + 46.1$. An output means is included for displaying the values calculated by the ratio calculating means and the stroke volume calculating means.

In a further embodiment of the present invention, an incremental storage means is included to generate a sum of the stroke volume over a period of time, thereby providing a measurement of the cardiac output of the individual. The monitoring device may further include an alarm means for signaling an alarm in the event that any of the calculated values differs from a desired range.

In the fullest embodiment of the present invention, the monitoring device still further includes a transmitting means for transmitting the values calculated by the monitoring device to a remote location.

BRIEF DESCRIPTION OF THE DRAWINGS

The present invention will be better understood when read in light of the accompanying drawings in which.

DESCRIPTION OF THE PREFERRED EMBODIMENT

Figure 1:
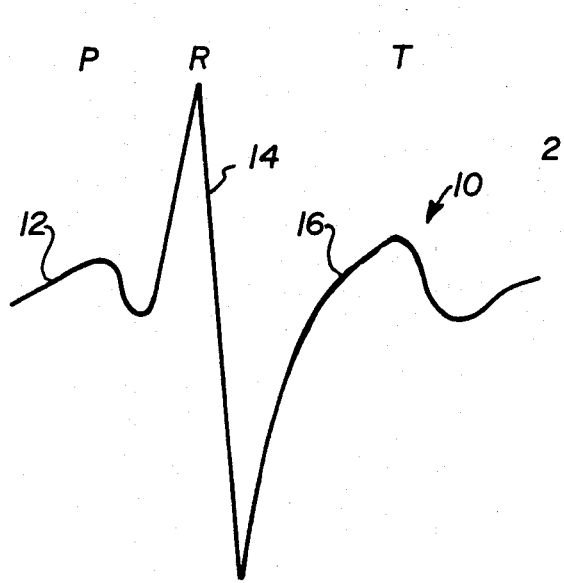
FIG. 1 is an illustration of a typical electrocardiogram waveform illustrating the component waves of which the waveform is comprised.

Referring to the illustration of FIG. 1, there is illustrated a typical electrocardiogram waveform 10 generated by a healthy individual at rest. The waveform is comprised of three component waves, the P-wave 12, the R-wave 14, and the T-wave 16. The amplitudes of the respective waves 12, 14, and 16 vary according to the amount of activity performed by the individual upon whom the electrocardiogram waveform 10 is obtained. It is from a similar such waveform 10 that the present invention obtains data in order to calculate the cardiac pumping performance of the individual.

Figure 2:
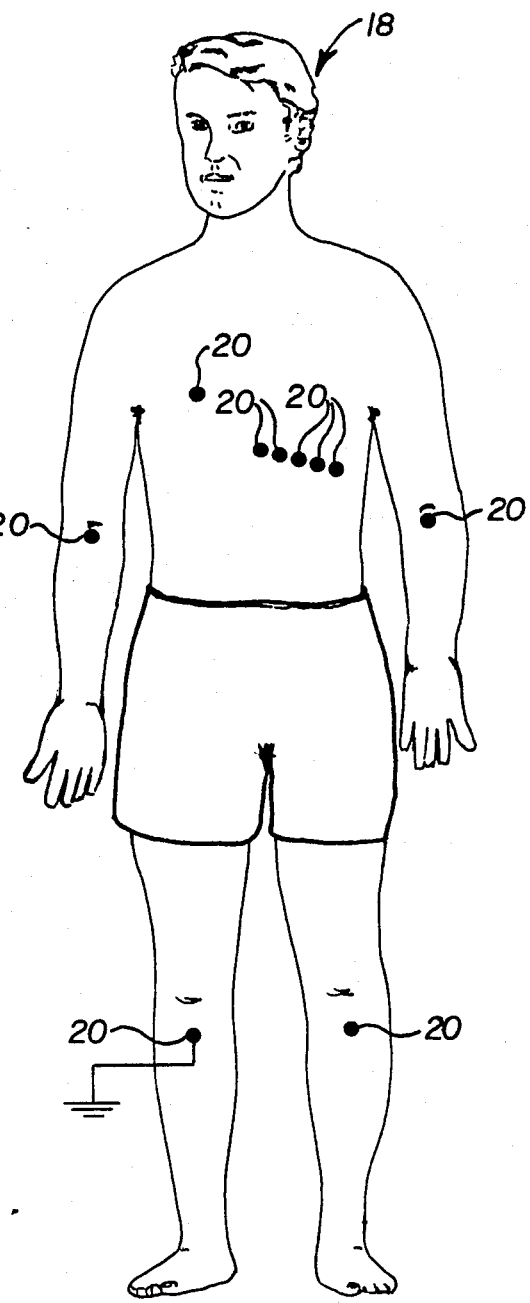
FIG. 2 illustrates a typical positioning configuration of a twelve lead electrocardiogram electrode configuration (ten leads including a ground line) on an individual to produce eleven waveforms similar to the waveform illustrated in FIG. 1.

Referring now to the illustration of FIG. 2, there is illustrated an individual 18 to whom a plurality of electrode leads 20 have been attached. Illustrated in FIG. 2 is the positioning of leads 20 of a typical twelve lead electrocardiogram. Ten leads 20 including one ground line, form twelve electrocardiogram waveform patterns, one of which is illustrated by the waveform 10 of FIG. 1.

Figure 3A:
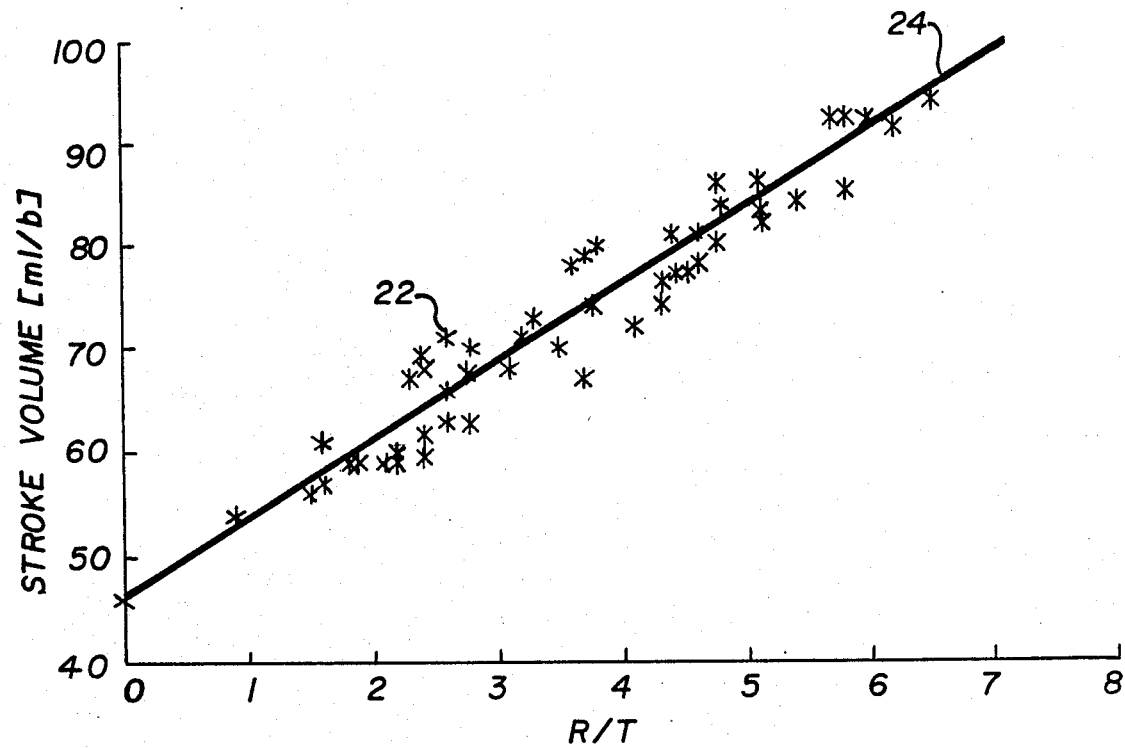
FIG. 3A is a graphical illustration of the relationship between the R/T ratio and the stroke volume for an individual.

Of importance to the present invention is the relationship between the amplitude of the R-wave 14 and T-wave 16. Upon evaluation of experimental data, it has been shown that there is a linear relationship between the ratio of the R-wave amplitude to the T-wave amplitude and the stroke volume of the individual 18. This relationship is illustrated in the graph of FIG. 3A. In the graph, numerous points 22 corresponding to experimentally derived correlations between the ratio of R/T are illustrated. Points 22 correlate to straight line 24 defined by the equation:

$$SV = 7.5 \times R/T + 46.1$$

wherein SV is the stroke volume of the individual, and R/T is the ratio of the R-wave component amplitude to the T-wave component amplitude. As previously mentioned, the stroke volume of an individual is the amount of blood pumped by the individual's heart in one heartbeat.

Figure 3B:
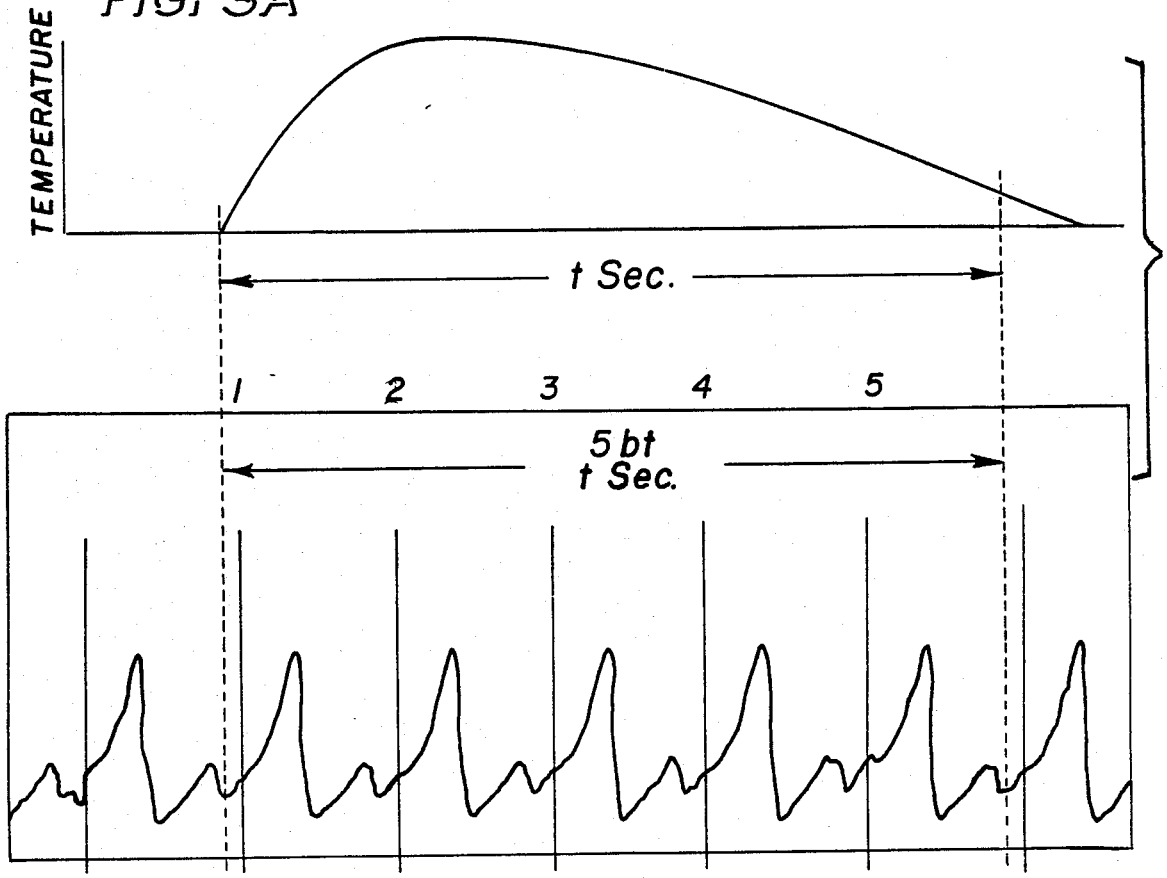
FIG. 3B is a graphical illustration of the temperature change of an individual's heart when a cold bolus is injected into the circulatory system.

This relationship may also be shown by utilizing data measured during practice of the previously mentioned thermodilution and dye method. Referring now to FIG. 3B, there is illustrated a plot of a typical temperature change of an individual's heart subsequent to the injection of a cold fluid into the bloodstream. By measuring the time t required for the temperature of the heart to recover, in FIG. 3B, the cardiac output for this period of time may be accurately calculated. By dividing this value by the number of heartbeats (as measured by an electrocardiogram), the stroke volume of the individual's heart may be calculated. The stroke volume calculated in this manner similarly correlates to line 24 of FIG. 3A.

Figure 4:
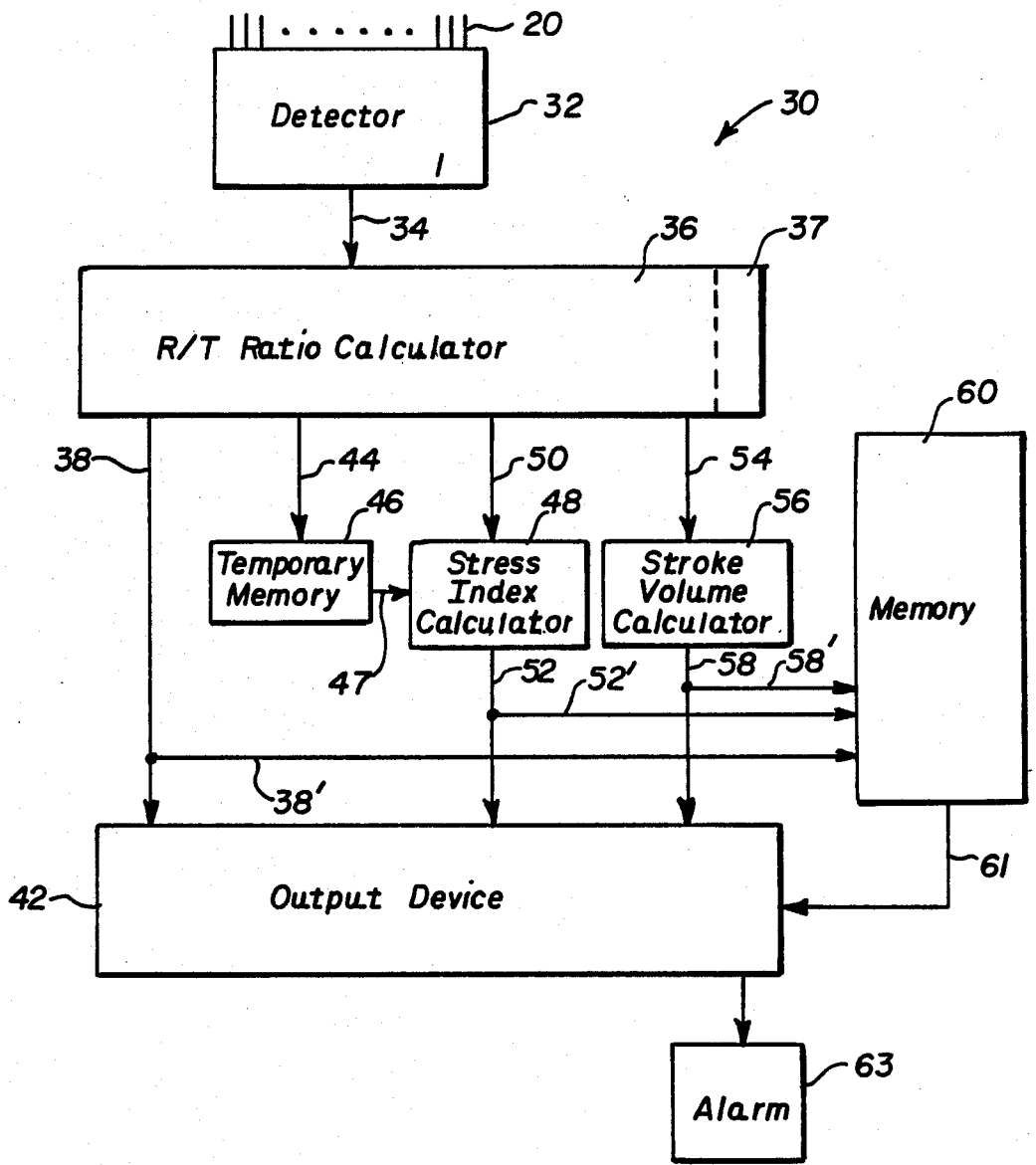
FIG. 4 is a block diagram of the cardiac performance monitoring device of the present invention.

Illustrated in of FIG. 4, is a block diagram of the cardiac performance monitoring device 30 of the present invention. Monitoring device 30 functions to calculate the stroke volume of the heart of an individual 18 when supplied with data concerning the waveform 10 of the electrocardiogram waveform of the individual 18. Electrocardiogram leads 20 are electrically connected to detector 32 of device 30. Detector 32 functions to measure the amplitudes of the R-wave and the T-wave components of each waveform 10 measured by each of the leads 20. Detector 32 selects the waveform 10 having a T-wave with the greatest amplitude and generates a signal on line 34 indicative of this waveform 10 having the greatest T-wave amplitude.

Line 34 is coupled to ratio calculator 36 which forms the numerical ratio of the amplitude of the R-wave to the amplitude of the T-wave. Calculator 36 generates a signal on line 38 indicative of this ratio.

In the event that a medical procedure is planned which would prevent the use of the electrode lead 20 associated with the waveform containing the maximum T-wave amplitude (such as sternotomy in which no electrodes are permitted to be positioned on areas of an individual's chest), calculator 36 calculates the ratio prior to commencement of the medical procedure. The value of this ratio is stored in local memory 37, and a waveform from any other electrode lead 20 may be standardized relative to the memorized value.

Line 38 is coupled to output device 42, which may be comprised of light emitting diodes, a line printer, or any other conventional interface apparatus.

The ratio calculated by ratio calculator 36 is further output on line 44 which is coupled to temporary memory location 46. Temporary memory 46 is, in turn, coupled, on line 47, to stress index calculator 48. Stress index calculator 48 is also supplied a signal indicative of the ratio calculated by ratio calculator 36 on line 50. Stress index calculator 48 determines the ratio between the signal supplied to it on line 47 and the signal supplied on line 50. This ratio is output on line 52 which is also coupled to output device 42.

The ratio calculated by ratio calculator 36 is further supplied on line 54 which is coupled to stroke volume calculator 56. The stroke volume calculator 56 calculates the stroke volume of the individual 18 according to the previously-mentioned regression equation. A signal indicative of the stroke volume is output on line 58 which is also coupled with output device 42. Signals generated on lines 38, 52, and 58 are also coupled to memory device 60 on lines 38', 52', and 58', respectively. Memory device 60 allows long-term storage of each of the values, and allows later display of these values on output device 42 by connection of memory device 60 through line 61. In the preferred embodiment, monitoring device 30 further includes alarm means 63 in order to generate an alarm in the event that any of the values calculated by monitoring device 30 differs from desired values.

Figure 5:
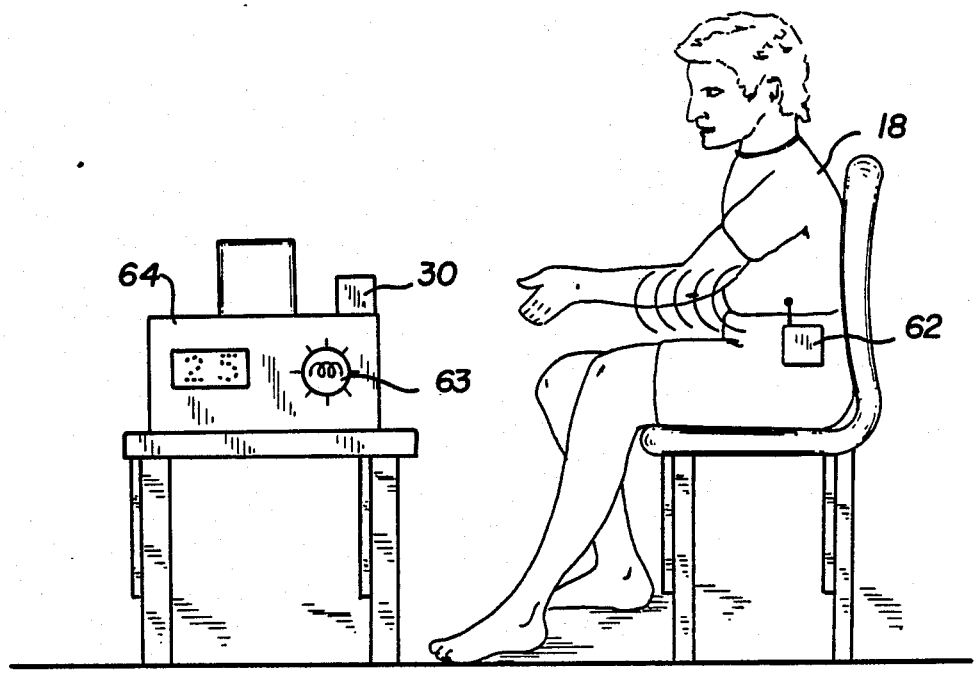
FIG. 5 is a schematic illustration of a further embodiment of the monitoring device of the present invention further including a transmitting means for transmitting the values calculated by the monitoring device to a remote location.

Referring now to the schematic illustration of FIG. 5, there is illustrated a further embodiment of the instant invention. In this embodiment, the signals needed by the cardiac performance monitoring device 30 to function are supplied by transmitter means 62 and receiver means 64. Receiver 64, connected to the cardiac monitoring device 30, allows remote monitoring of the cardiac functions of an individual 18. The monitoring device 30 may be positioned at the patient's bedside or at a remote location, for example, a central nurses's station. Cardiac monitoring device 30 contains alarm means 63 in order to generate an alarm in the event that any of the values calculated by monitoring device 30 differs from desired values.

In the embodiment of FIG. 5, monitoring device 30 may, for example, be utilized to monitor an individual 18 during post-operative care, and during therapeutic management of an individual. The monitoring device 30 and the receiver 64 may be positioned at a central nurse's station, and the information needed for calculation by the device 30 may be transmitted by transmitter 62 attached to the patient.

In a similar manner, monitoring device 30 may be adapted to function as an alarm device to generate alarms during sleep irregularities, such as sleep apnea.

In operation, cardiac performance monitoring device 30 functions to provide a quantitative evaluation of the cardiac pumping performance of an individual. Device 30 calculates quantitative information concerning the individual virtually instantaneously, and is of particular utility because the monitoring device allows calculation of the stroke volume of an individual during the performance of medical procedures, such as open heart surgery, and other times at which prior art devices were incapable of functioning. The device 30 further allows the effects of various procedures, such as induction of anesthesia, sternotomy, dissection, going-on bypass, and returning from bypass to be quantitatively measured and analyzed.

Figure 6:
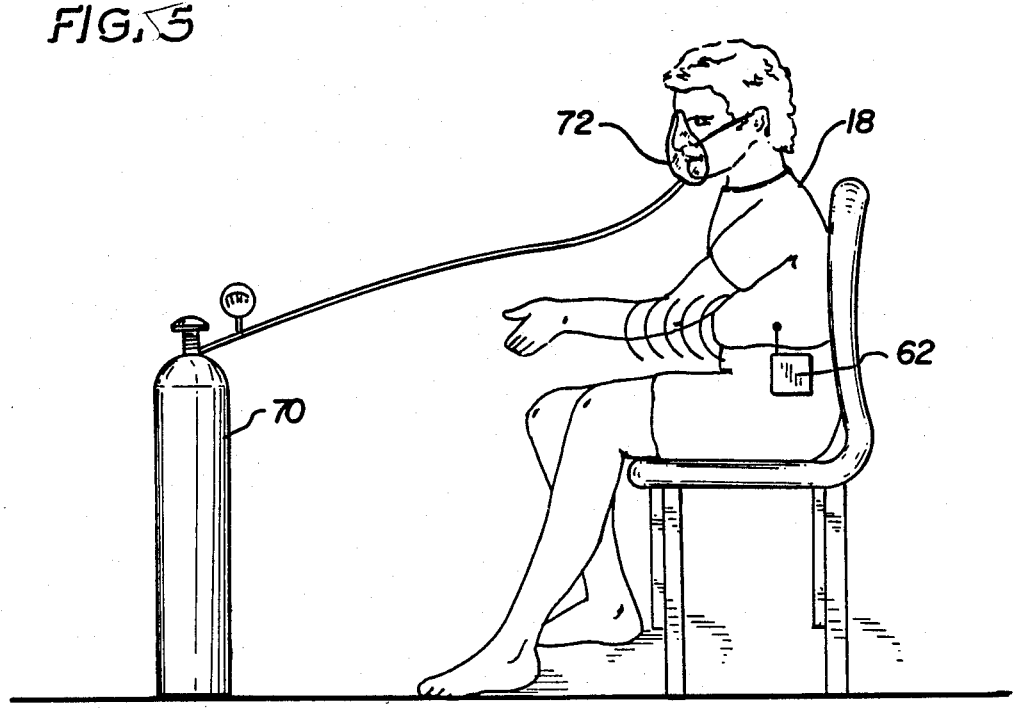
FIG. 6 is a schematic illustration of the monitoring device used by an individual in conjunction with a cardiovascular conditioning program.
Figure 7:
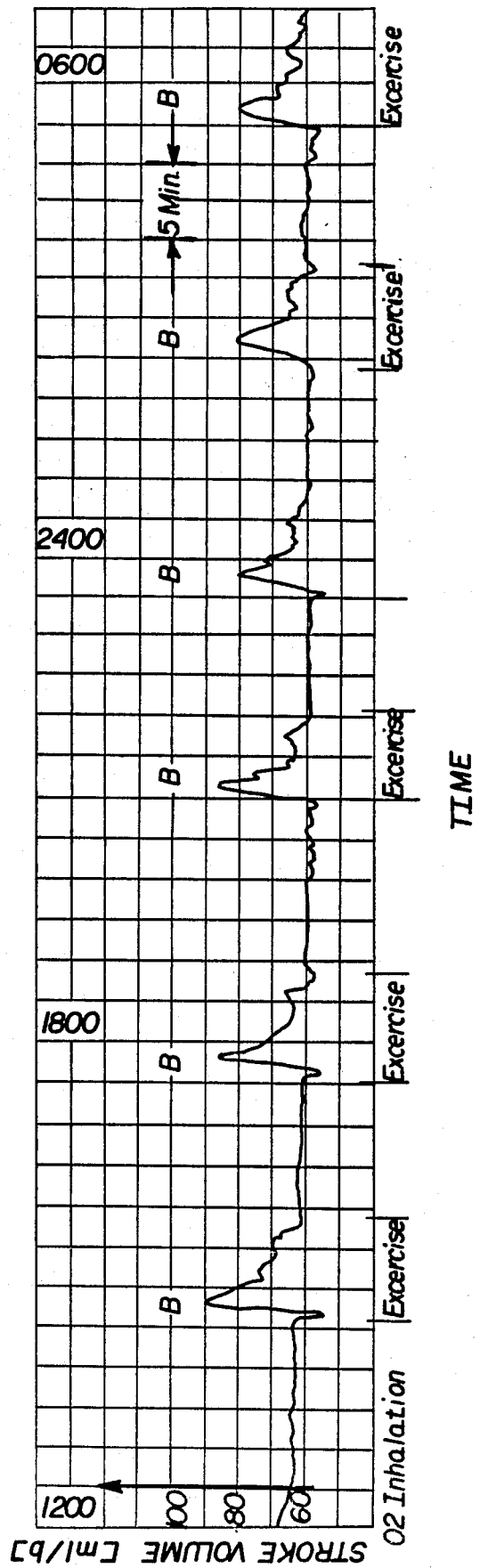
FIG. 7 is a waveform of the stroke volume data produced by the oxykinetics program.

Still further, monitoring device 30 may be utilized to monitor the individual 18 during oxygen inhalation and cardiovascular rehabilitation programs, such as an oxykinetic exercise program. Referring to the schematic illustration of FIG. 6, the cardiac performance monitoring device 30 together with transmitter 62 is utilized in order to monitor individual 18 during such exercise. The individual 18 is supplied an oxygen-air mixture from tank 70 through mask 72. The individual 18 then engages in intermittent periods of exercise, the intensity and duration of such exercise being controlled by the magnitude of the individual's stroke volume calculated by monitoring device 30 as illustrated in FIG. 7. Calculation of the individual's stroke volume may further be utilized to control the flow rate and oxygen concentration of the oxygen-air flow. Oxykinetic programs such as this aid in the improvement in cardiopulmonary performance to progressively elevate the maximum oxygen consumption of the individual 18, in some instances by as much as ten percent. Used in this manner, monitoring device 30 also functions as a safety device to prevent overexertion of the individual 18 during performance of cardiopulmonary rehabilitation programs.

While the present invention has been described in accordance with the preferred embodiments of the various figures, it is to be understood that other similar embodiments and other mathematical combinations of R-wave amplitude and T-wave amplitude and standardizations other than the largest T-wave may be used, or modifications and additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A non-invasive cardiac monitoring device for determining cardiac pumping performance of an individual, comprising:

electrocardiogram sensing means for sensing and generating a signal indicative of an electrocardiogram waveform of the individual;

R-wave amplitude measuring means for measuring the amplitude of an R-wave component of the electrocardiogram waveform;

T-wave amplitude measuring means for measuring the amplitude of a T-wave component of the electrocardiogram waveform;

ratio calculating means for determining the ratio of the amplitude of the R-wave component to the amplitude of the T-wave component and for generating a ratio signal indicative of said ratio;

stroke volume calculating means for generating a stroke volume signal indicative of the stroke volume of an individual as a function of said ratio signal generated by the ratio calculating means; and output means for displaying values of said ratio signal and said stroke volume signal.

2. The non-invasive cardiac monitoring device of claim 1 wherein said stroke volume calculating means generates the stroke volume signal according to the equation:

$$\text{stroke volume} = 7.5 * R/T + 46.1$$

wherein R/T = the value of the ratio signal generated by the ratio calculating means.

3. The non-invasive cardiac monitoring device of claim 2 further including memory means for storing values of said ratio signal and said stroke volume signal.

4. A non-invasive cardiac monitoring device according to claim 2 wherein said stroke volume calculation means includes means for generating a signal for monitoring said individual in a cardiac pulmonary rehabilitation program.

5. The non-invasive cardiac monitoring device of claim 1 wherein said electrocardiogram sensing means includes a multiple-lead electrocardiogram sensor.

6. The non-invasive cardiac monitoring device of claim 4 wherein saidelectrocardiogram sensing means further includes means for selecting the electrocardiogram waveform having a T-wave component of the greatest amplitude among the electrocardiogram waveforms detected by each of the multiple leads of the electrocardiogram sensor.

7. The non-invasive cardiac device of claim 1 further including incremental memory means for storing successive values of the stroke volume whereby the contents of the incremental memory means is indicative of the cardiac output of the individual.

8. A non-invasive cardiac monitoring device according to claim 1 further including means responsive to said electrocardiogram sensing means for supplying oxygen enriched air to an individual while exercising in a cardiac pulmonary rehabilitation program.

9. A method for monitoring the cardiac performance of an individual comprising the steps of:

obtaining an electrocardiogram waveform of the individual;

measuring the amplitude of an R-wave component of the electrocardiogram waveform;

measuring the amplitude of a T-wave component of the electrocardiogram waveform;

calculating a ratio of the amplitude of the R-wave component to the amplitude of the T-wave component; and calculating a value of stroke volume as a function of said ratio.

10. The method of claim 9 wherein the electrocardiogram waveform selected for said step of obtaining an electrocardiogram waveform is one waveform of a plurality of waveforms displaying the largest T-wave.

11. The method of claim 9 wherein the stroke volume is calculated according to the equation:

$$\text{stroke volume} = 7.5 * R/T + 46.1$$

wherein R/T = the ratio of the amplitude of the R-wave component to the amplitude of the T-wave component.

12. The method of claim 9 including the further step of calculating a value of cardiac output by summing successive values of stroke volume over sixty seconds.

13. The method according to claim 12 including the further step of using said stroke volume to generate a signal for a cardiac pulmonary rehabilitation program.

14. The method according to claim 9 including the further step of using said stroke volume to generate a signal for a cardiopulmonary rehabilitation program.

15. The method according to claim 9 including the further step of supplying oxygen enriched air to an individual while said individual is exercising to carryout a cardiac pulmonary rehabilitation program.

16. A method for monitoring the cardiac performance of an individual in a cardiac pulmonary rehabilitation program comprising the steps of:

obtaining an electrocardiogram waveform of the individual;

measuring the amplitude of an R-wave component of the electrocardiogram waveform;

measuring the amplitude of a T-wave component of the electrocardiogram waveform;

calculating a ratio of the R-wave component to the amplitude of the T-wave component;

calculating a value of stroke volume as a function of said ratio; and using said value of stroke volume to generate a signal for monitoring a cardiac pulmonary rehabilitation program for said individual.

17. The method according to claim 16 wherein said step of using said value of stroke volume includes controlling a supply of oxygen enriched air to said individual.

* * * * *